(12) United States Patent
Ghassemi-Armaki et al.

(10) Patent No.: US 12,345,696 B2
(45) Date of Patent: Jul. 1, 2025

(54) METHODS FOR INSPECTION OF PRESS-HARDENING STEEL SURFACES PRIOR TO SPOT-WELDING FOR IMPROVED WELDING QUALITY

(71) Applicant: GM GLOBAL TECHNOLOGY OPERATIONS LLC, Detroit, MI (US)

(72) Inventors: Hassan Ghassemi-Armaki, Northville, MI (US); Blair E. Carlson, Ann Arbor, MI (US); Zhenke Teng, Troy, MI (US); Jason M. Brown, Goodrich, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 427 days.

(21) Appl. No.: 17/872,222

(22) Filed: Jul. 25, 2022

(65) Prior Publication Data

US 2024/0027421 A1    Jan. 25, 2024

(51) Int. Cl.
| | | |
|---|---|---|
| *G01N 33/207* | (2019.01) | |
| *G01N 23/223* | (2006.01) | |
| *G01N 27/90* | (2021.01) | |
| *G01N 33/208* | (2019.01) | |
| *G06T 7/00* | (2017.01) | |
| *G06V 10/74* | (2022.01) | |

(52) U.S. Cl.
CPC ......... *G01N 33/207* (2019.01); *G01N 23/223* (2013.01); *G01N 27/90* (2013.01); *G01N 33/208* (2019.01); *G06T 7/001* (2013.01); *G06V 10/74* (2022.01); *G06T 2207/10064* (2013.01); *G06T 2207/10116* (2013.01); *G06T 2207/30136* (2013.01)

(58) Field of Classification Search
CPC .. G01N 33/207; G01N 33/208; G01N 23/223; G01N 27/90; G06V 10/74; G06T 7/001; G06T 2207/10064; G06T 2207/10116; G06T 2207/30136
See application file for complete search history.

(56) References Cited

U.S. PATENT DOCUMENTS

| | | |
|---|---|---|
| 7,999,243 B2 | 8/2011 | Rosinski |
| 8,087,298 B1 | 1/2012 | DiMambro et al. |
| 8,176,793 B2 | 5/2012 | Wang et al. |
| 8,222,896 B2 | 7/2012 | Dasch |
| 8,803,024 B2 | 8/2014 | Wang et al. |

(Continued)

*Primary Examiner* — Matthew C Bella
*Assistant Examiner* — Jinsu Hwang

(57) ABSTRACT

A method for inspecting a component made of press-hardening steel prior to resistance spot welding of the component includes performing non-destructive testing of the component made of press-hardening steel after hot stamping to determine a plurality of characteristics for the component. The non-destructive testing comprises at least one of image processing, electromagnetic analysis, and elemental analysis of the component. The method includes using a model correlating values of the characteristics to acceptable weld quality or rejected weld quality and predicting acceptable weld quality or rejected weld quality of the component prior to resistance spot welding of the component; resistance spot welding the component if the model predicts acceptable weld quality; and not resistance spot welding the component if the model predicts rejected weld quality.

20 Claims, 5 Drawing Sheets

(56) References Cited

U.S. PATENT DOCUMENTS

| | | | |
|---|---|---|---|
| 2004/0004183 A1* | 1/2004 | Grant | H01J 49/0409 |
| | | | 250/281 |
| 2016/0168975 A1* | 6/2016 | Donderici | G01N 27/90 |
| | | | 324/238 |
| 2021/0341451 A1* | 11/2021 | Maiorano | B23K 31/125 |
| 2023/0139733 A1* | 5/2023 | Mo | G01N 33/2045 |
| | | | 702/166 |

* cited by examiner

METHODS FOR INSPECTION OF PRESS-HARDENING STEEL SURFACES PRIOR TO SPOT-WELDING FOR IMPROVED WELDING QUALITY

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates to resistance spot welding, and more particularly to methods for inspecting press-hardening steel prior to resistance spot welding.

Manufacturers use hot-stamped press-hardening steel to make components for products such as vehicles. In some situations, a supplier of the press-hardening steel used by the manufacturer may vary over time.

When producing parts using press-hardening steel from different suppliers, variations in the alloying content and hot-stamping process can change one or more characteristics of a press-hardening steel surface. The variations in characteristics may lead to variability in response to a weld window for resistance spot welding. If the press-hardening steel is not suitable for the welding window, the weld nugget may be too small or too large and/or expulsion events may occur.

Expulsion events involve ejection of a portion of molten metal from a molten nugget during resistance spot welding. Expulsion events cause weld thinning and voids at the center of the nugget. This in turn causes significant degradation of weld strength.

For press-hardening steel using aluminum-silicon (Al—Si) coatings that are very brittle, the expulsion events may cause burrs and/or whiskers to form on the weld surface. Burrs and whiskers are unacceptable when manufacturing certain types of components.

SUMMARY

A method for inspecting a component made of press-hardening steel prior to resistance spot welding of the component includes performing non-destructive testing of the component made of press-hardening steel after hot stamping to determine a plurality of characteristics for the component. The non-destructive testing comprises at least one of image processing, electromagnetic analysis, and elemental analysis of the component. The method includes using a model correlating values of the characteristics to acceptable weld quality or rejected weld quality and predicting acceptable weld quality or rejected weld quality of the component prior to resistance spot welding of the component; resistance spot welding the component if the model predicts acceptable weld quality; and not resistance spot welding the component if the model predicts rejected weld quality.

In other features, the non-destructive testing comprises image processing. The image processing comprises taking an image of at least a portion of the component; comparing the image of the component to a plurality of stored images corresponding to different types of coatings; identifying a type of coating of the component in response to the comparison; and selectively accepting or rejecting the component at least in part based the identification.

In other features, the non-destructive testing comprises electromagnetic analysis. The electromagnetic analysis comprises inducing eddy currents in the component at a plurality of different frequencies to measure a plurality of resistance values at different layers of the component.

In other features, the method includes generating a difference between a first one of the plurality of resistance values and a sum of two or more of the plurality of resistance values; comparing the difference to a predetermined threshold; and accepting or rejecting the component at least in part based on the comparison.

In other features, the non-destructive testing comprises elemental analysis of at least one coating of the component. The elemental analysis comprises x-ray fluorescence. The elemental analysis comprises laser elemental analysis.

In other features, the non-destructive testing comprises image processing, electromagnetic analysis and elemental analysis; image processing of the component is configured to identify a coating type of an oxide layer of the component; electromagnetic analysis of the component includes inducing eddy currents at a plurality of frequencies to determine resistances of a plurality of layers of the component; and elemental analysis of the component includes using at least one of x-ray fluorescence and laser elemental analysis to determine a composition of at least one coating of the component.

A method for inspecting a component made of press-hardening steel prior to resistance spot welding of the component includes performing non-destructive testing of a plurality of components made of press-hardening steel after hot stamping to determine a plurality of characteristics for each of the plurality of components. The non-destructive testing comprises at least one of image processing, electromagnetic analysis, and elemental analysis of the plurality of components. The method includes storing the plurality of characteristics for the plurality of components; resistance spot welding the plurality of components; inspecting weld quality of the plurality of components; and based on the weld quality and the plurality of characteristics of the plurality of components, generating a model configured to predict acceptable and rejected weld quality of the component prior to resistance spot welding of the component.

In other features, the non-destructive testing comprises image processing. The image processing comprises taking an image of at least one portion of the plurality of components; comparing the image of the at least one portion of the plurality of components to a plurality of stored images corresponding to different types of coatings; identifying a type of coating in response to the comparison; and selectively accepting or rejecting the at least one of the plurality of components at least in part based the identification.

In other features, the non-destructive testing comprises electromagnetic analysis. The electromagnetic analysis comprises inducing eddy currents in the component at a plurality of different frequencies to measure a plurality of resistance values at different layers of the component.

In other features, the method includes generating a difference between a first one of the plurality of resistance values and a sum of two or more of the plurality of resistance values; comparing the difference to a predetermined threshold; and accepting or rejecting the component at least in part based on the comparison.

In other features, the non-destructive testing comprises elemental analysis of the plurality of components. The elemental analysis comprises x-ray fluorescence. The elemental analysis comprises laser elemental analysis.

In other features, the non-destructive testing comprises the image processing, the electromagnetic analysis, and the elemental analysis; the image processing is configured to identify a coating type of an oxide layer of the component; the electromagnetic analysis includes inducing eddy currents at a plurality of frequencies to determine resistances of a plurality of layers of the component; and the elemental analysis of the component includes using at least one of x-ray fluorescence and laser elemental analysis.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

In the drawings, reference numbers may be reused to identify similar and/or identical elements.

DETAILED DESCRIPTION

While the foregoing description describes inspection methods for inspecting press-hardening steel prior to resistance spot welding (RSW) in the context of manufacturing of components of vehicles, the methods can also be used for other types of components for non-vehicle applications.

The methods described herein relate to prediction of weld quality for variations in hot-stamped press-hardening steel. The prediction is based on results of image processing of the steel surface and other types of non-destructive testing (NDT) of a coating of the steel before resistance spot-welding (RSW) is performed. The method determines characteristics of the hot-stamped press-hardening steel component and generates a decision to accept (likely within the welding window used for the resistance spot welding) or reject (likely outside of the welding window used for the resistance spot welding) the hot-stamped press-hardening steel components prior to resistance spot welding.

Figure 1:
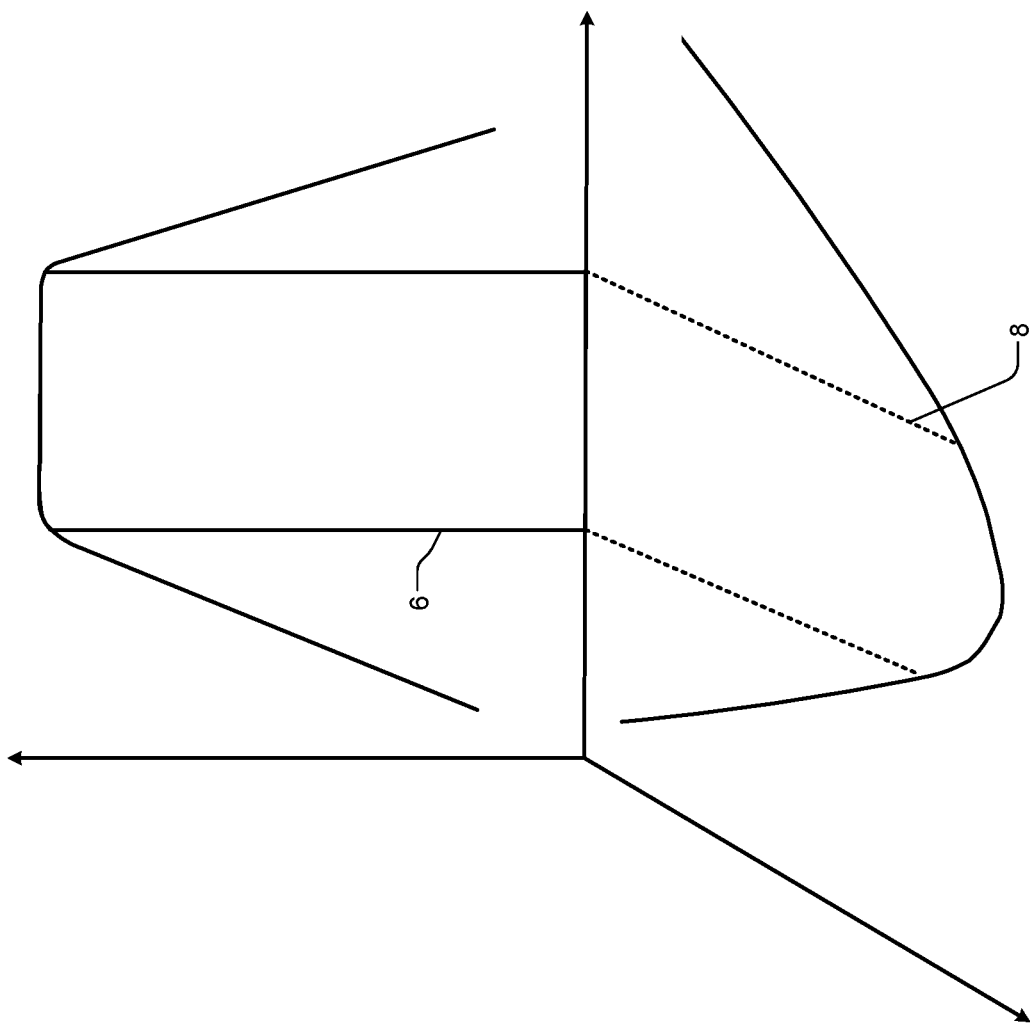
FIG. 1 is a graph illustrating base metal mechanical properties and weld quality as a function of coating characteristic parameters.

Referring now to FIG. 1, base metal mechanical properties of press-hardening steel can be optimized using a variety of iron, aluminum, silicon, and oxide (Fe—AlSiO) coating characteristic parameter(s). However, an optimized zone 6 with respect to the base metal mechanical properties is not the same as an optimized zone 8 for weld quality. The optimized zone 8 for weld quality has a different shape as shown in FIG. 1 and is more sensitive to changes in Fe—AlSiO coating characteristic parameter(s). Therefore, a sample of press-hardening steel that meets the base metal mechanical properties criteria may or may not produce welds with acceptable weld quality.

Figure 2:
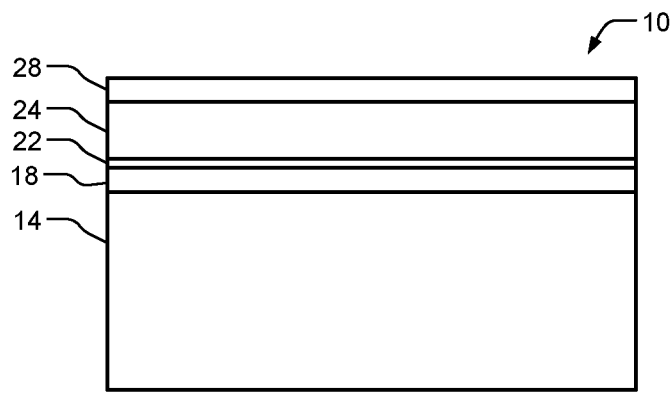
FIGS. 2 to 4 are enlarged side cross-sectional views of examples of samples of press-hardening steel.
Figure 3:
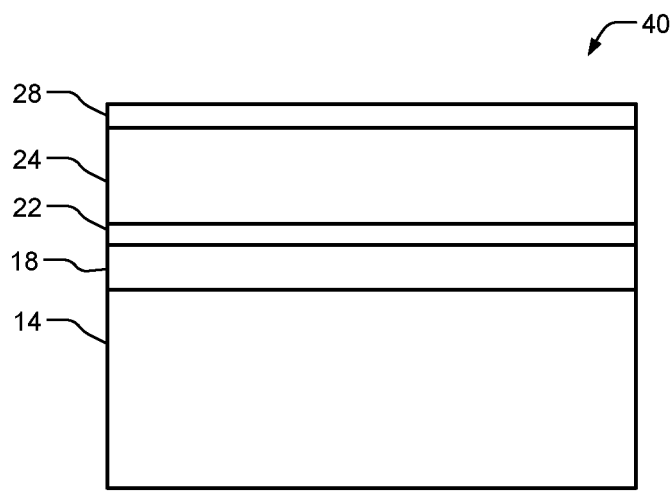
Figure 4:
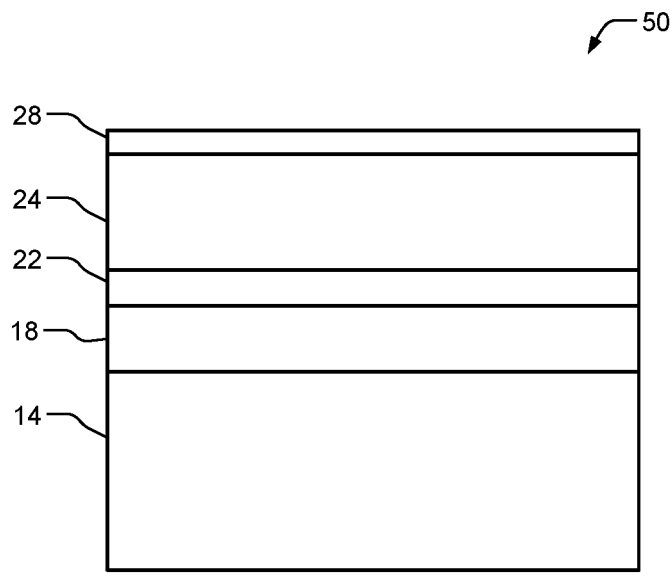

Referring now to FIGS. 2-4, variations in coating layers in press-hardening steel samples after hot-stamping are shown. In FIGS. 2 to 4, different samples of press-hardening steel 10, 40 and 50 are shown after hot-stamping and include a steel substrate 14, an Alpha-Fe diffusion interlayer 18, an iron-aluminum alloy (FeAl) layer 22, a layer 24 including a combination of intermetallic components, and an oxide layer 28. In some examples, one or more of the layers may have different compositions and/or thicknesses that may affect weld quality despite meeting the base metal mechanical properties criteria.

In some examples of the present disclosure, the method analyzes layers of samples of the press-hardening steel 10, 40 and 50 to predict characteristics of the press-hardening steel 10, 40 and 50 that likely correspond to acceptable weld quality (and conversely those corresponding that likely correspond to rejected weld quality). Changes in coating characteristics after hot-stamping may occur due to variations in initial thickness and/or alloying elements of the coating, and/or variations in heat-treatment conditions. As can be appreciated, the thicknesses and/or compositions of the layers may vary from one supplier to another due to variability of the steel coating from the steel making process (before the hot-stamping process) or from the hot-stamping process conditions.

In some examples, the inspection method according to the present disclosure relies upon three layers of the press-hardening steel including: the Alpha-Fe diffusion interlayer 18, the layer 24 including the combination of intermetallic components, and the oxide layer 28.

More particularly, the press-hardening steel 10, 40 and 50 is analyzed using steel surface image processing, electromagnetic analysis, and/or elemental analysis. The steel surface image processing is used to analyze characteristics of the oxide layer 28. The electromagnetic analysis is used to analyze the Alpha-Fe diffusion interlayer 18, the layer 24 including the combination of intermetallic components, and/or the oxide layer 28. The elemental analysis is used to analyze the layer 24 including the combination of intermetallic components and/or the oxide layer 28.

For example, it may be determined after analysis that the press-hardening steel 10 (FIG. 2) and 50 (FIG. 3) are likely to be out of the welding window (and should be rejected) and the press-hardening steel 40 (FIG. 2) is likely to be in the welding window (and should be accepted). The welding window may be defined by the power level (e.g., maximum amplitude of welding current), the shape of the welding current waveform (e.g., rise time, fall time, and transitions of leading and/or trailing edges of the current waveform), duration (e.g., on time) that welding is performed using the welding electrodes, and/or other welding parameters.

Referring now to FIGS. 5 to 7B, a method 310 for building a model for inspection of hot-stamped press-hardening steel is shown. At 314 in FIG. 5, the method may be performed after hot-stamping of the press-hardening steel. At 318, image processing of the press-hardening steel is performed. Visual characteristics of the oxide layer 28 are analyzed using image processing.

Figure 6:
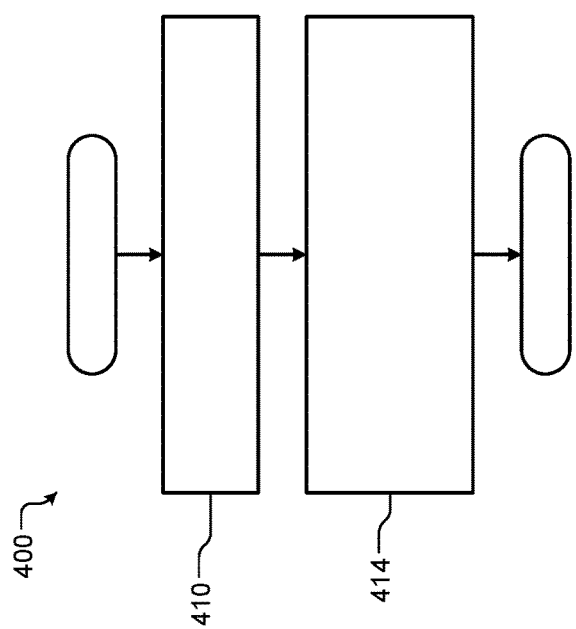
FIG. 6 is a method for performing image analysis of press-hardening steel according to the present disclosure.

In an example of an image processing method 400 in FIG. 6, an image of the press-hardening steel is generated at 410. Using image processing, the image is compared to images of different types of coatings at 414. In some examples, the different types of coatings correspond to differences in color, although other characteristics can be used. The image processing determines characteristics such as identification of a type of the oxide coating based on the color.

Figure 5:
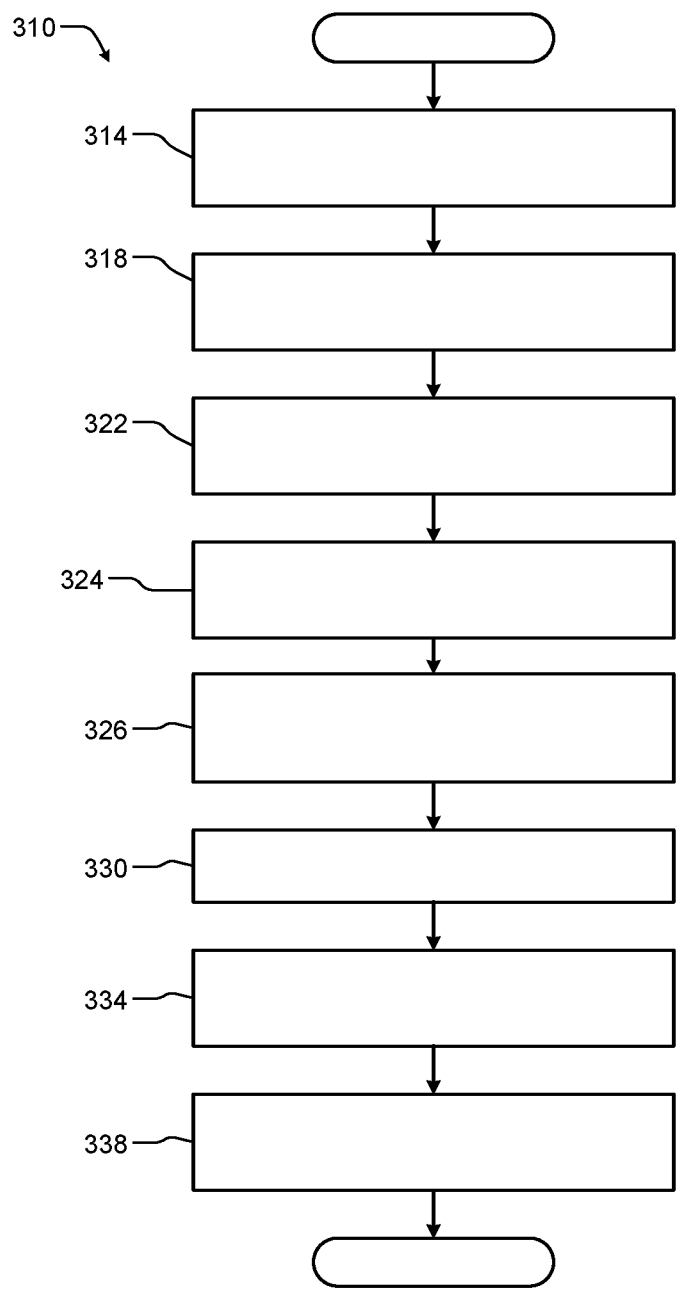
FIG. 5 is a flowchart of an example of a method for developing a model correlating characteristics of press-hardening steel that are measured using image processing, electromagnetic analysis and/or elemental analysis to weld quality according to the present disclosure.
Figure 7A:
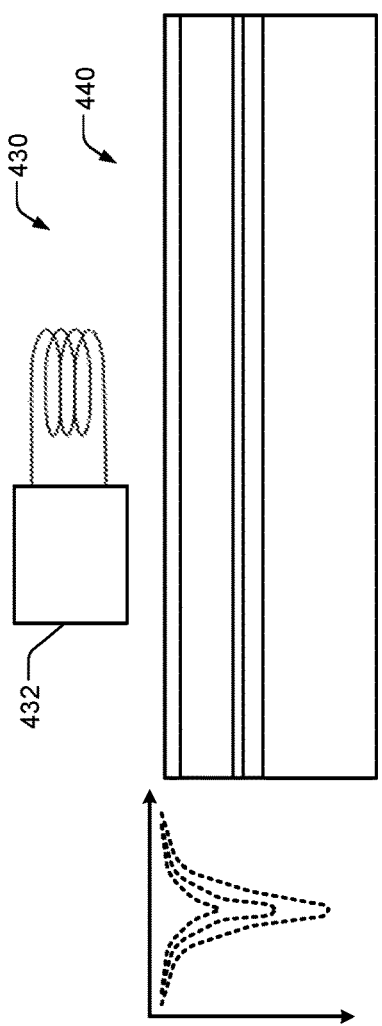
FIG. 7A is a functional block diagram illustrating a coil and power supply for performing electromagnetic analysis of press-hardening steel according to the present disclosure.
Figure 7B:
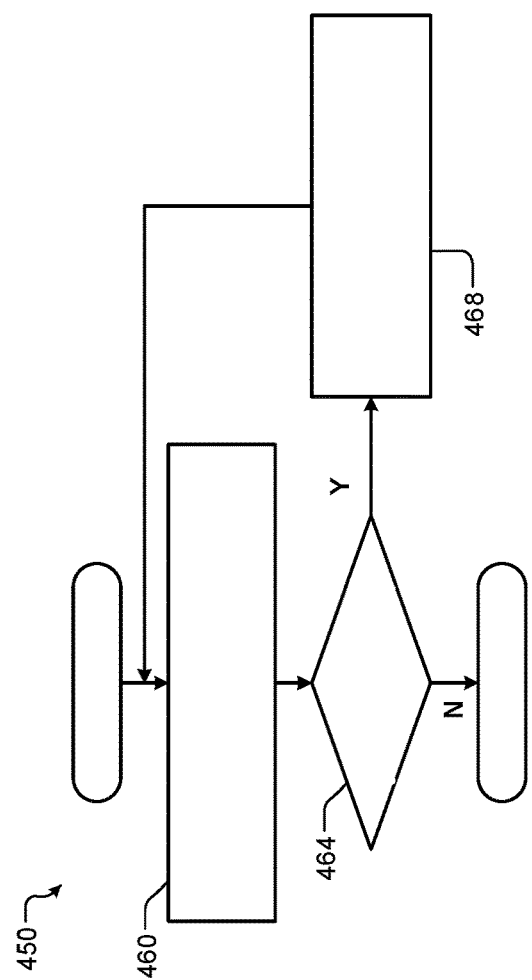
FIG. 7B is a method for performing electromagnetic analysis of press-hardening steel according to the present disclosure.

At 322 in FIG. 5, electromagnetic properties of the press-hardening steel are measured and analyzed. For example in FIGS. 7A and 7B, a coil 430 and radio frequency (RF) power source 432 are used to induce eddy currents in press-hardening steel 440. The coil 430 is arranged adjacent to the press-hardening steel 440 and the RF power source 432 outputs RF power at a predetermined frequency to the coil 430 to induce eddy currents in the press-hardening steel 440. The predetermined frequency can be varied to analyze materials at different depths of the press-hardening steel.

For example, a first frequency can be used to determine the resistivity of the oxide layer 28. A second frequency can be used to determine the resistivity of the layer 24 including the combination of intermetallic components. A third frequency can be used to determine the resistivity of the Alpha-Fe diffusion interlayer 18. In this example, the third frequency is higher than the second frequency and the second frequency is higher than the first frequency.

At 324 in FIG. 5, elemental analysis of the press-hardening steel is performed and analyzed. For example, x-ray fluorescence (XRF) may be used to determine elemental composition. XRF relies upon the process of ionization. Atoms within the sample material are ionized when exposed to gamma rays or other short-wavelength x-ray beams. Elemental composition is determined by measuring a secondary x-ray beam, corresponding to the fluorescent x-ray, emitted from the tested sample when it is excited by a primary x-ray source.

An XRF device includes a detector and an x-ray source. During analysis, an x-ray beam is directed at the press-hardening steel. When the initial x-ray beam hits the press-hardening steel, the atoms in the sample produce a fluorescent x-ray beam that is then processed by the detector. Differences in the energy emitted from both the initial and the fluorescence x-ray beams are associated with specific elements under analysis. In other examples, other elemental testing is performed. For example, laser elemental analysis (LEA) can be performed to determine composition of the component.

At 326, resistance spot welding (RSW) is performed on the press-hardening steel using a welding process window. At 330, the quality of the welds is checked and accepted or rejected. For example, the weld nugget size is within a predetermined window (between minimum and maximum nugget size). For example, the welds are also inspected to identify burrs and/or whiskers. For example, the welds are also inspected for weld strength.

At 334, a model is built to correlate measured characteristics with accepted and rejected welds. For example, the characteristics of the accepted welds are used to define acceptable ranges for the characteristics. At 338, the model is used to accept or reject the press-hardening steel prior to resistance spot welding (RSVV) based on the measured characteristics.

Figure 8:
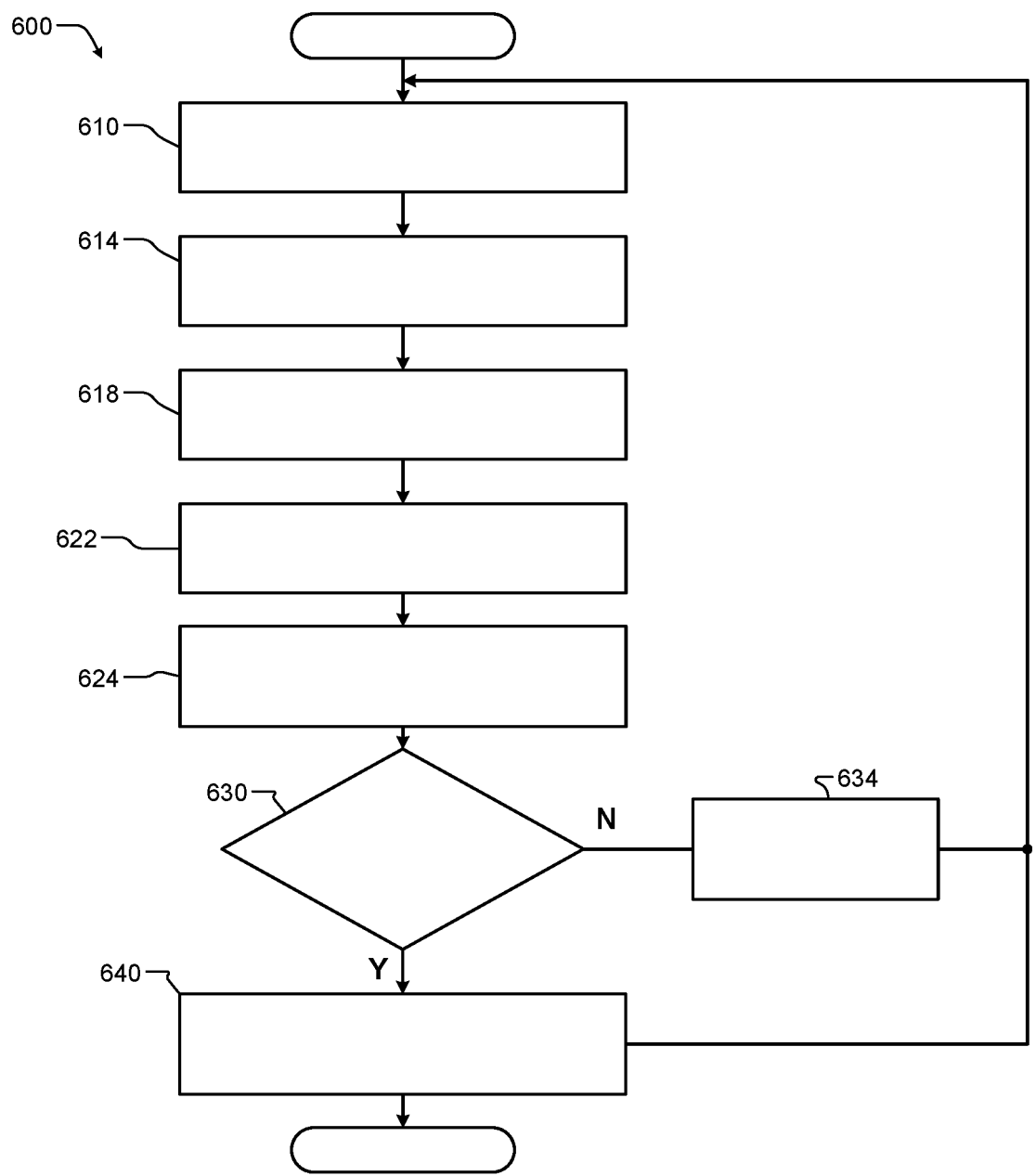
FIG. 8 is a flowchart of a method using the inspection model and characteristics measured using image processing, electromagnetic analysis and/or elemental analysis to predict weld quality of a press-hardening steel.

Referring now to FIG. 8, after the model is developed, it can be used to accept or reject subsequent samples of the press-hardening steel prior to resistance spot welding. In FIG. 8, an inspection method 600 optionally includes performing hot stamping of press-hardening steel at 610.

Characteristics of a sample of the press-hardening steel are determined using non-destructive testing. At 614, image processing of the press-hardening steel is performed. At 618, electromagnetic properties of the press-hardening steel are analyzed. At 622, elemental analysis of the press-hardening steel is performed. At 624, characteristics of the press-hardening steel are compared to characteristics and/or ranges of parameters defined by the model.

With respect to image processing, the color of the press-hardening steel is compared to predetermined colors corresponding to different types of coatings. If the color of the press-hardening steel matches first types of coatings that are acceptable then the press-hardening steel is accepted (subject to other characteristics). If the color of the press-hardening steel matches second types of coatings that are not acceptable (or does not match any coating) then the press-hardening steel is rejected.

With respect to electromagnetic characterization, in some examples, a first difference or delta (e.g., absolute value) between the resistance of the oxide layer and a sum of the resistance of the oxide layer and the layer 24 are determined. When the first difference or delta is equal to a first predetermined value or within a first predetermined window, the press-hardening steel is accepted (subject to other characteristics). When the difference or delta is greater than or less than the first predetermined value or outside the first predetermined window, the press-hardening steel is rejected.

In some examples, a second difference or delta in the resistivity of the oxide layer and a sum of the oxide layer 28, the layer 24 and the Alpha-Fe diffusion interlayer 18 is determined. When the second difference or delta is equal to a second predetermined value or within a second predetermined window, the press-hardening steel is accepted. When the second difference or delta is greater than or less than the second predetermined value or outside the second predetermined window, the press-hardening steel is rejected.

In some examples, total Fe, a ratio of Fe/Al, and a ratio of Fe/(Al+Si) are determined using elemental analysis. When the total Fe (or normalized Fe) is equal to a third predetermined value or within a third predetermined window, the press-hardening steel is accepted based on the total Fe (subject to other characteristics). When the total Fe is not equal to the third predetermined value or not within the third predetermined window, the press-hardening steel is rejected based on total Fe. Likewise, when the ratio of Fe/Al is equal to a fourth predetermined value or within a fourth predetermined window, the press-hardening steel is accepted based on the ratio of Fe/Al (subject to other characteristics). When the ratio of Fe/Al is not equal to the fourth predetermined value or not within the fourth predetermined window, the press-hardening steel is rejected based on the ratio of Fe/Al. Likewise, when the ratio of Fe/(Al+Si) is equal to a fifth predetermined value or within a fifth predetermined window, the press-hardening steel is accepted based on ratio of Fe/(Al+Si) (subject to other characteristics). When ratio of Fe/(Al+Si) is not equal to the fifth predetermined value or not within the fifth predetermined window, the press-hardening steel is rejected based on the ratio of Fe/(Al+Si).

At 630, the method determines whether the characteristics are within range for the welding process window that is being used. If 630 is true, resistance spot welding is performed using the welding process window. If 630 is false, the press-hardening steel is rejected at 634.

The method according to the present disclosure inspects press-hardening steel after hot-stamping to determine whether it is suitable for the welding window used by a resistance spot-weld process. A model is developed that correlates measured characteristics (based on nondestructive testing of a steel surface (such as image analysis, electromagnetic analysis, and/or elemental analysis)) to characteristics of press-hardening steel having acceptable welds using the welding window. The method also uses image analysis to determine whether the press-hardening steel has a non-optimal coating, which is an indicator that the press-hardening steel will be out of the welding window. The analysis is performed before the press-hardening steel is resistance spot-welded.

In some examples, the method determines a minimum Al—Si—Fe—O coating thickness and minimum Alpha-Iron diffusion layer thickness for the resistance spot-weld process to allow a minimum weld nugget size to be achieved. In some examples, the method determines a maximum Al—Si—Fe—O coating thickness and maximum Alpha-Fe diffusion layer thickness for the resistance spot-weld process to avoid burrs and surface whiskers on the surface of the press-hardening steel that is in contact with an electrode.

Advantages of the method according to the present disclosure include reduced time required for inspection during hot-stamping production (less than 5 min). The method enables automated inspection of every part versus destructive inspection of selected parts. The method relies upon automated inspection and not upon human-knowledge based judgment after destructive coating inspection. The method can be used to inspect all surfaces of a component and flanges rather than selective surfaces of the component using destructive metallography. The method correlates metallurgy, coating, surface quality and image processing characteristics to optimize the resistance spot welds.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A method for inspecting a component made of press-hardening steel prior to resistance spot welding of the component, comprising:
   performing non-destructive testing of the component made of press-hardening steel after hot stamping to determine a plurality of characteristics for the component,
   wherein the non-destructive testing comprises at least one of image processing, electromagnetic analysis, and elemental analysis of the component;
   using a model correlating values of the characteristics to acceptable weld quality or rejected weld quality and predicting acceptable weld quality or rejected weld quality of the component prior to resistance spot welding of the component;
   resistance spot welding the component if the model predicts acceptable weld quality; and
   not resistance spot welding the component if the model predicts rejected weld quality.

2. The method of claim 1, wherein the non-destructive testing comprises image processing.

3. The method of claim 2, wherein the image processing comprises:
   taking an image of at least a portion of the component;
   comparing the image of the component to a plurality of stored images corresponding to different types of coatings;
   identifying a type of coating of the component in response to the comparison; and
   selectively accepting or rejecting the component at least in part based the identification.

4. The method of claim 1, wherein the non-destructive testing comprises electromagnetic analysis.

5. The method of claim 4, wherein the electromagnetic analysis comprises inducing eddy currents in the component at a plurality of different frequencies to measure a plurality of resistance values at different layers of the component.

6. The method of claim 5, further comprising:
   generating a difference between a first one of the plurality of resistance values and a sum of two or more of the plurality of resistance values;
   comparing the difference to a predetermined threshold; and
   accepting or rejecting the component at least in part based on the comparison.

7. The method of claim 1, wherein the non-destructive testing comprises elemental analysis of at least one coating of the component.

8. The method of claim 7, wherein the elemental analysis comprises x-ray fluorescence.

9. The method of claim 7, wherein the elemental analysis comprises laser elemental analysis.

10. The method of claim 1, wherein:
    the non-destructive testing comprises image processing, electromagnetic analysis and elemental analysis;
    image processing of the component is configured to identify a coating type of an oxide layer of the component;
    electromagnetic analysis of the component includes inducing eddy currents at a plurality of frequencies to determine resistances of a plurality of layers of the component; and
    elemental analysis of the component includes using at least one of x-ray fluorescence and laser elemental analysis to determine a composition of at least one coating of the component.

11. A method for inspecting a component made of press-hardening steel prior to resistance spot welding of the component, comprising:
    performing non-destructive testing of a plurality of components made of press-hardening steel after hot stamping to determine a plurality of characteristics for each of the plurality of components,
    wherein the non-destructive testing comprises at least one of image processing, electromagnetic analysis, and elemental analysis of the plurality of components;
    storing the plurality of characteristics for the plurality of components;
    resistance spot welding the plurality of components;
    inspecting weld quality of the plurality of components; and
    based on the weld quality and the plurality of characteristics of the plurality of components, generating a model configured to predict acceptable and rejected weld quality of the component prior to resistance spot welding of the component.

12. The method of claim 11, wherein the non-destructive testing comprises image processing.

13. The method of claim 12, wherein the image processing comprises:
    taking an image of at least one portion of the plurality of components;

comparing the image of the at least one portion of the plurality of components to a plurality of stored images corresponding to different types of coatings;

identifying a type of coating in response to the comparison; and selectively accepting or rejecting the at least one of the plurality of components at least in part based the identification.

14. The method of claim 11, wherein the non-destructive testing comprises electromagnetic analysis.

15. The method of claim 14, wherein the electromagnetic analysis comprises inducing eddy currents in the component at a plurality of different frequencies to measure a plurality of resistance values at different layers of the component.

16. The method of claim 15, further comprising:

generating a difference between a first one of the plurality of resistance values and a sum of two or more of the plurality of resistance values;

comparing the difference to a predetermined threshold; and accepting or rejecting the component at least in part based on the comparison.

17. The method of claim 11, wherein the non-destructive testing comprises elemental analysis of the plurality of components.

18. The method of claim 17, wherein the elemental analysis comprises x-ray fluorescence.

19. The method of claim 17, wherein the elemental analysis comprises laser elemental analysis.

20. The method of claim 11, wherein:

the non-destructive testing comprises the image processing, the electromagnetic analysis, and the elemental analysis;

the image processing is configured to identify a coating type of an oxide layer of the component;

the electromagnetic analysis includes inducing eddy currents at a plurality of frequencies to determine resistances of a plurality of layers of the component; and the elemental analysis of the component includes using at least one of x-ray fluorescence and laser elemental analysis.

* * * * *